United States Patent [19]

Gillett et al.

[11] Patent Number: 5,659,042

[45] Date of Patent: Aug. 19, 1997

[54] METHOD FOR PREPARING ESTERS OF HALONICOTINIC ACIDS

[75] Inventors: Samuel J. Gillett, Albany; Michael E. Garst, Newport Beach; Alan T. Johnson, Rancho Santa Margarita, all of Calif.

[73] Assignee: Allergan, Waco, Tex.

[21] Appl. No.: 329,023

[22] Filed: Oct. 25, 1994

[51] Int. Cl.[6] .................................................. C07D 213/30
[52] U.S. Cl. .................................................... 546/318
[58] Field of Search .......................................... 546/318

[56] References Cited

U.S. PATENT DOCUMENTS

| | | | |
|---|---|---|---|
| 4,576,629 | 3/1986 | Morland et al. | 546/175 |
| 5,023,341 | 6/1991 | Chandraratna | 546/164 |
| 5,089,509 | 2/1992 | Chandraratna | 514/337 |

OTHER PUBLICATIONS

Yamanaka et al, Site–Selectivity in the Reaction of 3–Substituted Pyridine 1–Oxides with Phosphoryl Chloride, Chemical Pharmaceutical Bulletin, 36(6) 2244–2247 (1988).

Trujillo et al, Facile Esterification of Sulfonic Acids and Carboxylic Acids with Triethylorthoacetate, Tetrahedron Letters, vol. 34, No. 46, pp. 7355–7358, 1993.

March, Advanced Organic Chemistry: Reactions, Mechanism, and Structure, 1968 by Mcgraw–Hill Inc. p. 21. 1968.

*Primary Examiner*—Jane Fan
*Attorney, Agent, or Firm*—Robert J. Baran; Martin A. Voet; Howard R. Lambert

[57] ABSTRACT

The present invention provides a method of preparation of ethyl 6-halonicotinate, wherein said halo is chloro or iodo, which comprises reacting the 6-halonicotinic acid with triethyl orthoacetate, to yield the ethyl-6-halonicotinate.

12 Claims, No Drawings

METHOD FOR PREPARING ESTERS OF HALONICOTINIC ACIDS

BACKGROUND OF THE INVENTION

1. Field of the Invention

The invention relates to the preparation of halo nicotinic acid esters which are useful in preparing compounds having retinoid activity, e.g. 6-[2-(4,4-dimethylthiochroman-6-yl) ethynyl]nicotinate.

2. Background of the Art

6-[2-(4,4-dimethylthiochroman-6-yl)ethynyl]nicotinate is a compound which is known to have retinoid activity, i.e. it is active at the same biological receptor as retinoic acid. This compound is disclosed in U.S. Pat. No. 5,089,509. In this patent, 6-[2-(4,4-dimethylthiochroman-6-yl)ethynyl] nicotinate is prepared by the reaction of 4,4-dimethyl-6-ethynyl-thiochroman and ethyl-6-chloronicotinate. In this patent ethyl-6-chloronicotinate is prepared by the reaction of 6-chloronicotinic acid and ethanol in the presence of dicyclohexylcarbodiimide and dimethylaminopyridine, dissolved in methylene chloride. The yield in this preparation is only about 60% and the workup is very difficult. In addition, the reagents used in this synthesis (1,3-dicyclohexylcarbodiimide and 4-dimethylaminopyridine) are identified as Highly Toxic (USA) and Toxic (European) (Source: Aldrich Material Data Safety [MDS] Sheet). As a result these reagents pose a considerable health risk before, during, and after the reaction is conducted. In U.S. Pat. No. 5,023,341, it is also disclosed that 6-[2-(4,4-dimethylthiochroman-6-yl)ethynyl]nicotinate may be prepared by the above reaction.

6-ethyl chloronicotinate is prepared from the corresponding 6-chloronicotinic acid and ethanol in U.S. Pat. No. 4,576,629. The nicotinate is utilized to prepare various herbicides. In this reference, a yield of 89% was obtained by means of a large excess of ethanol and sulfuric acid as the catalyst for the esterification reaction. This procedure requires a difficult separation of the product as well as requiring the handling of a very corrosive sulfuric acid reactant. Sulfuric acid is also identified as being Highly Toxic (MDS sheet). Further, it cannot be disposed of until it is neutralized with base. The procedure will result in added health risks and cost.

Chloronicotinic acid esters are also prepared by the reaction of 3-substituted pyridine-1-oxides with phosphoryl chloride. (See Yamanaka et al, Site-Selectivity in the Reaction of 3-Substituted Pyridine 1-Oxides with Phosphoryl Chloride; *Chem. Pharm. Bull.* 36(6)2244–2247(1988)). The procedure results in a mixture 2 and 6-chloronicotinic acid esters which must be separated to obtain the 6-chloronicotinic acid ester prepared according to the process of the present invention. Moreover, the 6-chloro is present as a minor component in the isomer mixture.

The unsubstituted compound, nicotinic acid, has been esterified by reaction with triethylorthoacetate at a yield of 80%. (See Trujillo et al, Facile Esterification of Sulfonic Acids and Carboxylic Acids with Triethylorthoacetate; *Tetrahydro Letters*, Vol. 34, No. 46, pp. 7355–7358, (1993)). Unexpectedly, the applicant's have achieved significantly higher yields in the esterification of halonicotinic acids.

Thus, it is clear that there is a continuing interest in preparing esters of both substituted and nonsubstituted nicotinic acid which are useful as intermediates to prepare retinoids as well as other compounds.

It is therefore one object in the invention to provide a method of preparing an ethyl-6-halonicotinate in high yield.

It is another object to the present invention to provide such ethyl-6-halonicotinate in a process wherein an excess of reactants are not required, the product is isolated without difficulty and no corrosive reactants are utilized.

Additional objects, advantages and features of the invention will become apparent to those skilled in the art from the following description.

SUMMARY OF THE INVENTION

The present invention provides a method of preparing ethyl-6-halonicotinate that is 6chloronicotinate or 6-iodonicotinate, which comprises reacting the 6-halonicotinic acid with triethylorthoacetate to yield the corresponding ethyl-6-halonicotinate. The ratio of the 6-halonicotinic acid and triethylorthoacetate may vary from 1:10 to 1:1, preferably from 1:3 to 1:1.5. The present reaction may be carried out in the presence of a hydrocarbon diluent which is a liquid at the temperature of the reaction. Preferably, a slurry of the 6-chloronicotinic in an anhydrous hydrocarbon diluent, for example toluene, is stirred and triethylorthoacetate is added to the slurry dropwise. The resulting mixture may be warmed to reflux and then allowed to cool after the reaction has been effected. The resulting solution may be washed with an aqueous liquid to separate a ethyl-6-halonicotinate containing organic phase from the reaction mixture. The organic phase may be heated under conditions wherein the unreacted organics and the organic by-products are removed overhead to recover the ethyl-6-halonicotinate as an oil.

DETAILED DESCRIPTION OF THE INVENTION

The present invention may be represented by the following reaction scheme (I).

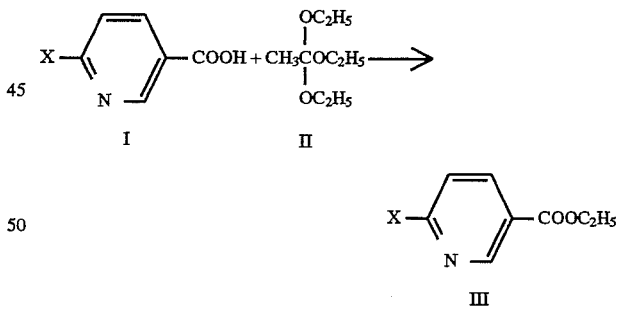

wherein X is chloro or iodo.

The resulting Compound III may be reacted to provide a retinoid according to the following Scheme (II)

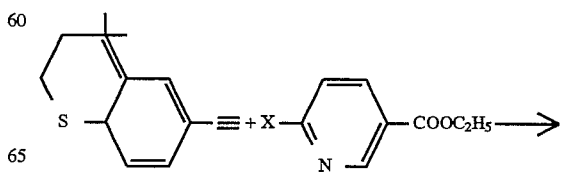

-continued

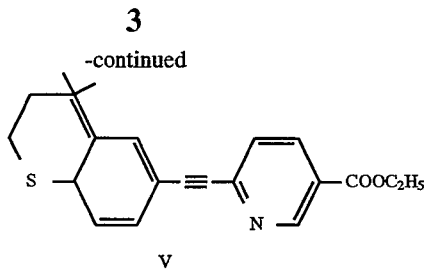

V

See U.S. Pat. Nos. 5,089,509 and 5,264,578 which are hereby incorporated by reference to show the preparation of the retinoid of formula V.

The invention is further illustrated by the following Examples which are illustrative of a specific mode of practicing the invention and are not intended as limiting the scope of the appended claim.

EXAMPLE 1

Ethyl 6-chloronicotinate

To a slurry of 6-chloronicotinic acid (5.0 g, 31.73 mmol) in anhydrous toluene (35 ml), was added dropwise with stirring triethylorthoacetate (15.45 g, 95.2 mmol). The mixture was warmed to reflux for two hours, allowed to cool to ambient temperature, and then the resultant solution was washed with saturated $NaHCO_3$ solution (50 ml). The organic phase was dried ($MgSO_4$) and the solvent removed in vacuo to afford the titled compound as a clear, colorless oil (5.43 g, 29.27 mmol, 92.3% yield).

EXAMPLE 2

Ethyl 6-iodonicotinate

Using the same procedure for ethyl 6-chloronicotinate but instead using 6-iodonicotinic acid (7.14 g, 28.67 mmol) and triethylorthoacetate (13.96 g, 86.02 mmol) gave the titled compound as a white solid (7.340 g, 26.49 mmol, 92.4%).

EXAMPLE 3

Ethyl 2-[2-(4,4-dimethylthiochroman-6-yl)-ethyn-1-yl]-5-nicotinate

A mixture of 0.632 g (2.75 mmol) of (4,4-dimethylthiochroman-6-yl) acetylene, 64 mg (0.33 mmol) of copper (I) iodide, and 5.08 g (50.3 mmol) of triethylamine are degassed with argon for 15 minutes. To the suspension is added 0.83 g (3.00 mmol) of ethyl 6-iodo-nicotinate and then 0.15 g (0.22 mmol) of Bis(triphenylphosphine) palladium (II) chloride. The suspension is degassed with argon for an additional 5 minutes, the tube is sealed and the mixture is stirred at 55° C. for 16 hours.

The mixture is cooled to room temperature and filtered through celite and silica gel using 200 mL of hexane and 20 mL of ethyl acetate. The solvents are removed in-vacuo and the residual oil is purified by flash chromatography ($SiO_2$, 5% ethyl acetate in hexanes) to give the title compound which is an active retinoid compound.

All particular embodiments of the invention have been described and it will be understood, of course, that the invention is not limited thereto. Since many obvious modifications can be made and it is intended to include within this invention any such modifications as will fall within the scope of the appended claims. Having now described the invention.

We claim:

1. A method of preparation of ethyl 6-halonicotinate, wherein said halo is chloro or iodo, which comprises reacting the 6-halonicotinic acid with triethylorthoacetate, to yield the ethyl-6-halonicotinate.

2. The method of claim 1 wherein the reaction is effected in the presence of a liquid hydrocarbon.

3. The method of claim 2 wherein said 6-halonicotinic acid is present as a slurry in the reaction mixture.

4. The method of claim 3 wherein said liquid hydrocarbon is toluene.

5. The method of claim 3 wherein said reaction is effected by the heating of the slurry to reflux.

6. The method of claim 5 wherein said 6-halonicotinic acid is 6-chloronicotinic acid.

7. The method of claim 5 wherein said 6-halonicotinic acid is 6-iodonicotinic acid.

8. The method of claim 1 wherein the ratio of 6-halonicotinic acid and triethylorthoacetate in the reaction mixture is from 1:3 to 1:1.5.

9. The method of claim 2 which further comprises separating the ethyl 6-halonicotinate from the reaction mixture by washing the reaction mixture with an aqueous solution to obtain ethyl-6-halonicotinate-containing organic phase and an aqueous phase.

10. The method of claim 9 further comprising separating ethyl-6-halonicotinate from said organic phase by distilling off the hydrocarbon liquid, the unreacted ethylorthoacetate and the organic by-products of the reaction to obtain the ethyl-6-halonicotinate as an oil.

11. The method of claim 10 wherein said aqueous solution is a saturated solution of $NaHCO_3$.

12. The method of claim 11 further comprising drying the organic phase over $MgSO_4$ prior to distillation.

* * * * *